US00PP34206P2

(12) United States Plant Patent
Sundermeyer

(10) Patent No.: US PP34,206 P2
(45) Date of Patent: May 10, 2022

(54) APPLE TREE NAMED 'SUNSPARK'

(50) Latin Name: *Malus domestica* *Borkh.*
Varietal Denomination: SunSpark

(71) Applicant: Li Imke GbR, Augsburg (DE)

(72) Inventor: Gerhard Sundermeyer, Ottbergen (DE)

(73) Assignee: LI IMKE GBR, Augsburg (DE)

( * ) Notice: Subject to any disclaimer, the term of this patent is extended or adjusted under 35 U.S.C. 154(b) by 0 days.

(21) Appl. No.: 17/208,857

(22) Filed: Mar. 22, 2021

(51) Int. Cl.
*A01H 5/08* (2018.01)
*A01H 6/74* (2018.01)

(52) U.S. Cl.
USPC ..... Plt./161
CPC ..... *A01H 6/7418* (2018.05)

(58) Field of Classification Search
USPC ..... Plt./161, 172
CPC ..... A01H 5/0875
See application file for complete search history.

(56) References Cited

U.S. PATENT DOCUMENTS

PP7,197 P 3/1990 Luby
PP17,201 P3 11/2006 Nicolai

OTHER PUBLICATIONS

PLUTO UPOVROM Plant Variety Database 20210624 citation for 'Sunspark' as per QZ PBR 20182023; Dec. 16, 2018; 1 page.*
CPVO (2018). "Application Form: *Malus domestica* Borkh.," CPVO, 6 pages.
CPVO (2018). "Official Gazette of the Community of Plant Variety Office," CPVO, Issue 6, 187 pages.
CPVO (2018). "Technical Questionnaire: *Malus domestica* Borkh.," CPVO, 6 pages.
CPVO (2020). "Official Gazette of the Community of Plant Variety Office," CPVO, Issue 5, 170 pages.

* cited by examiner

*Primary Examiner* — Kent L Bell
(74) *Attorney, Agent, or Firm* — Morrison & Foerster LLP

(57) ABSTRACT

A new and distinctive variety of a *Malus domestica* Borkh. apple tree named 'Sun Spark', particularly characterized by its fruit taste, crispy and juicy texture, with a sub-acid flavor and mild aroma with a sweet hue, as well as its long shelf-life, is disclosed.

6 Drawing Sheets

Botanical classification: *Malus domestica* Borkh.

Varietal denomination: The varietal denomination of the claimed apple tree variety is 'SunSpark'.

BACKGROUND OF THE INVENTION

Apples are an economically important crop. Accordingly, there exists a need to develop new varieties of apple tree with improved characteristics, such as fruit appearance and quality.

BRIEF SUMMARY OF THE INVENTION

In order to meet these needs, the present invention is directed to an improved variety of apple tree. In particular, the invention relates to a new and distinct variety of apple tree (*Malus domestica* Borkh.), which has been denominated as 'SunSpark'.

This new and distinct cultivar was discovered by the inventor as a chance seedling between many seedlings in the possession of the inventor in Ottbergen, Germany in October 2012. The inventor asexually reproduced the chance seedling by propagating several cuttings onto M9 rootstocks, and then selected the instant tree in the third year (second yield) from among several propagated test trees that originated from the original seedling.

The parents of 'SunSpark' were not known by the inventor. A molecular DNA study showed that the parents are 'Nicoter' (U.S. Plant Pat. No. 17,201) and 'Honeycrisp' (U.S. Plant Pat. No. 7,197). Therefore, 'SunSpark' originated as a seedling among many seedlings from a chance crossing of 'Nicoter' (U.S. Plant Pat. No. 17,201) and 'Honeycrisp' (U.S. Plant Pat. No. 7,197). It is unknown which parentage is the female and male parent of 'SunSpark'. 'Nicoter' (U.S. Plant Pat. No. 17,201) originated as a controlled cross between 'Gala' (unpatented) and 'Braeburn' (unpatented). 'Honeycrisp' (U.S. Plant Pat. No. 7,197) originated as a cross of known parentage 'Keepsake' (unpatented) and 'MN 1627' (unpatented).

The 'SunSpark' variety was selected for its taste. The fruits of this variety have a crispy and juicy texture, with a sub-acid flavor and mild aroma with a sweet hue. The fruit flesh is cream coloured and coarse in texture. The apples can be stored for a long time. Hardness hardly decreases during shelf life. The skin has 70-90% solid to mottled red coloration over a yellow background, with greater coloration if the fruit is more exposed to the sun. Lenticels are small but prominently visible. The fruit surface has shallow dimples and some green/golden russeting at the stem end.

Asexual reproduction of the 'SunSpark' apple tree variety as described herein shows that the foregoing and all other characteristics and distinctions are true to type and are established and transmitted through succeeding asexual propagations.

Parentage: 'Nicoter' (U.S. Plant Pat. No. 17,201) and 'Honeycrisp' (U.S. Plant Pat. No. 7,197).

Botanical Classification: *Malus domestica* Borkh.

The variety 'SunSpark' has been asexually propagated by chip budding and bench grafting onto virus free M9 (clone T 337) and MM 11 rootstocks in Swalmen, The Netherlands. The source of genetic reproduction material for propagation of the variety 'SunSpark' is maintained in The Netherlands.

Trees and fruits have demonstrated that the combination of characteristics as herein disclosed for the new variety 'SunSpark' are firmly fixed and remain true to type through successive generations of asexual reproduction.

Locality where grown and observed: Geldermalsen, The Netherlands. Trees grafted on M9 rootstock were planted in winter 2017-2018. Trees were trained as slender spindle, with a planting distance of 3.20 m by 1.00 m and with drip irrigation and fertigation.

Furthermore, a PCR virus test of the variety 'SunSpark' in The Netherlands showed that the trees are free of Apple dimple fruit viroid (ADFVd) and free of Apple scar skin viroid (ASSVd).

BRIEF DESCRIPTION OF THE DRAWINGS

The 'SunSpark' apple tree variety is illustrated by the accompanying photographs. The colors shown are as true as can be reasonably obtained by conventional photographic procedures. However, the colors in the photographs may vary with lighting conditions and, therefore, color characteristics of this new variety should be determined with reference to the observations described herein, rather than from the photographs alone. The photographs are from trees that are 3 years old.

DETAILED BOTANICAL DESCRIPTION

Figure 1:
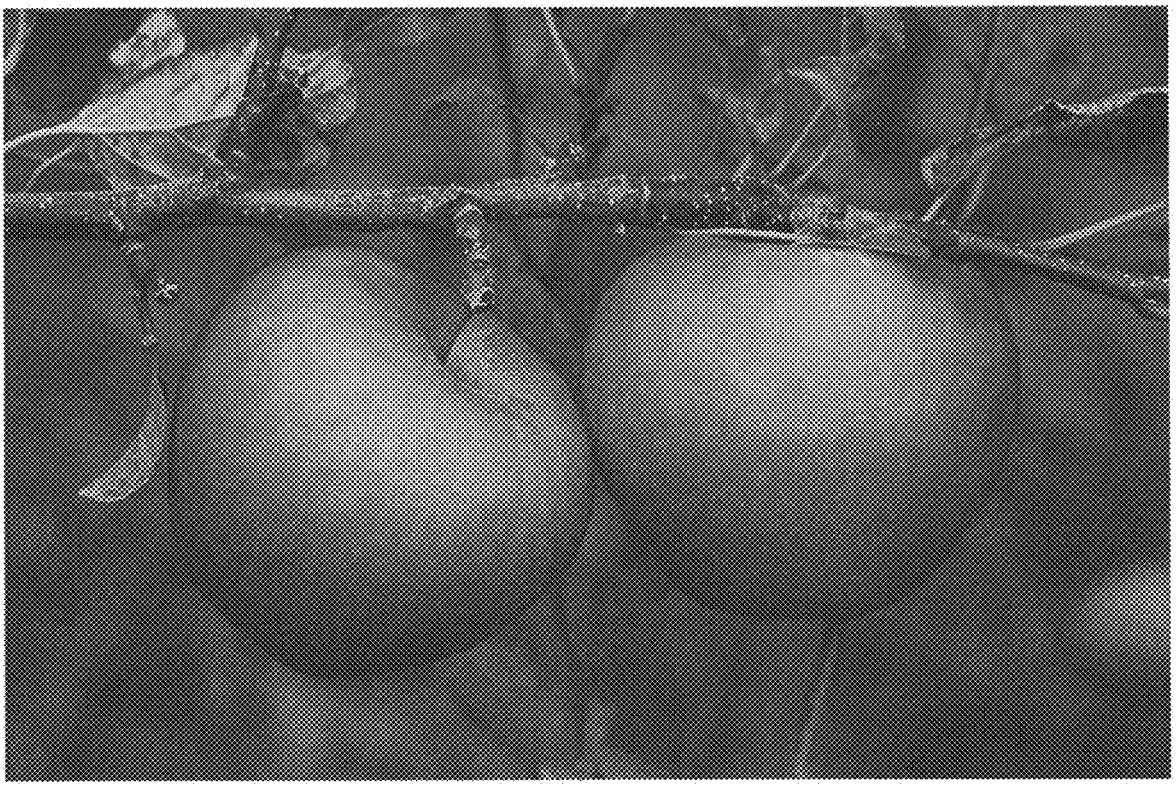
FIG. 1 illustrates fruits of apple tree variety 'SunSpark' prior to harvest.
Figure 2:
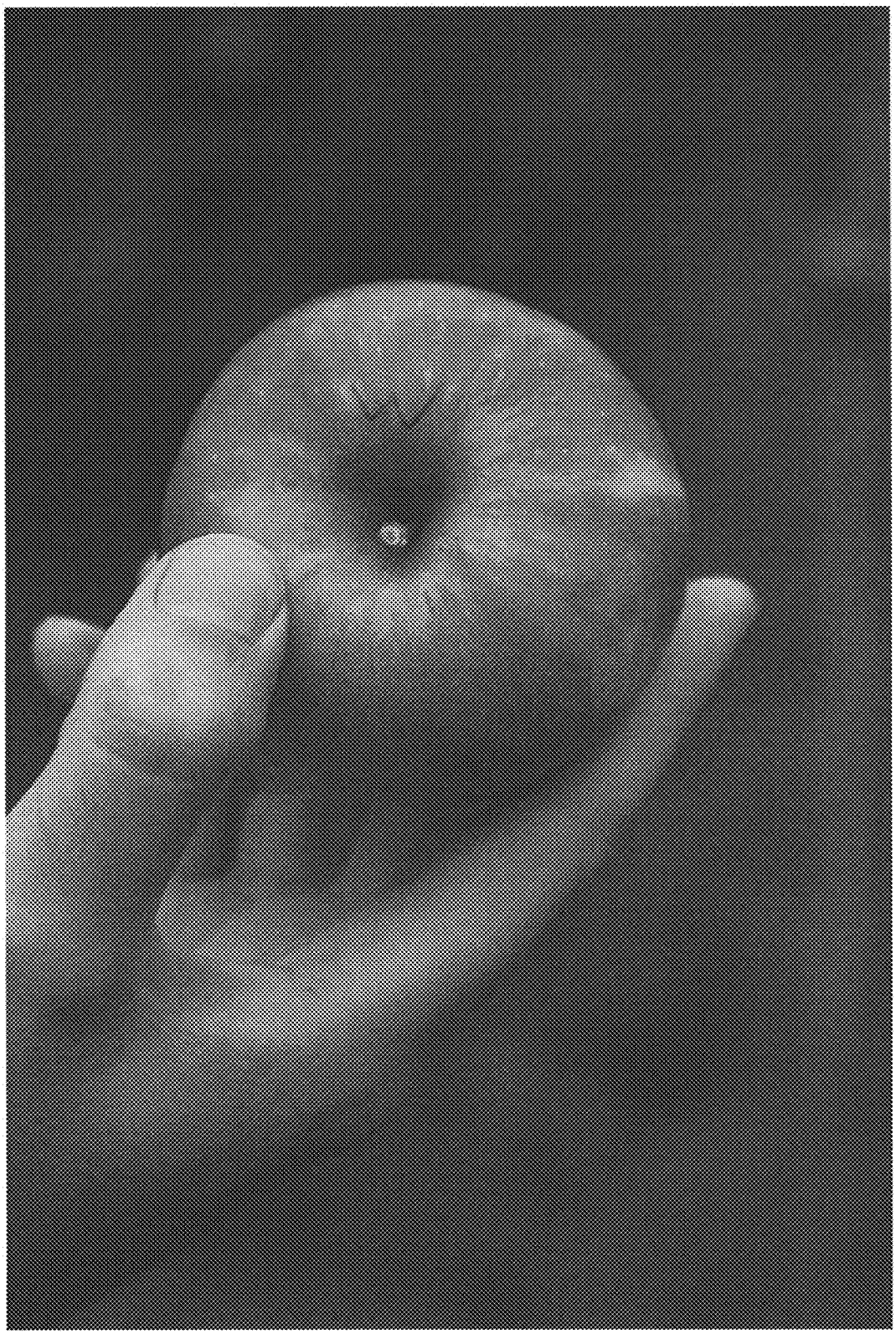
FIG. 2 illustrates a fruit of apple tree variety 'SunSpark' at harvest.
Figure 3:
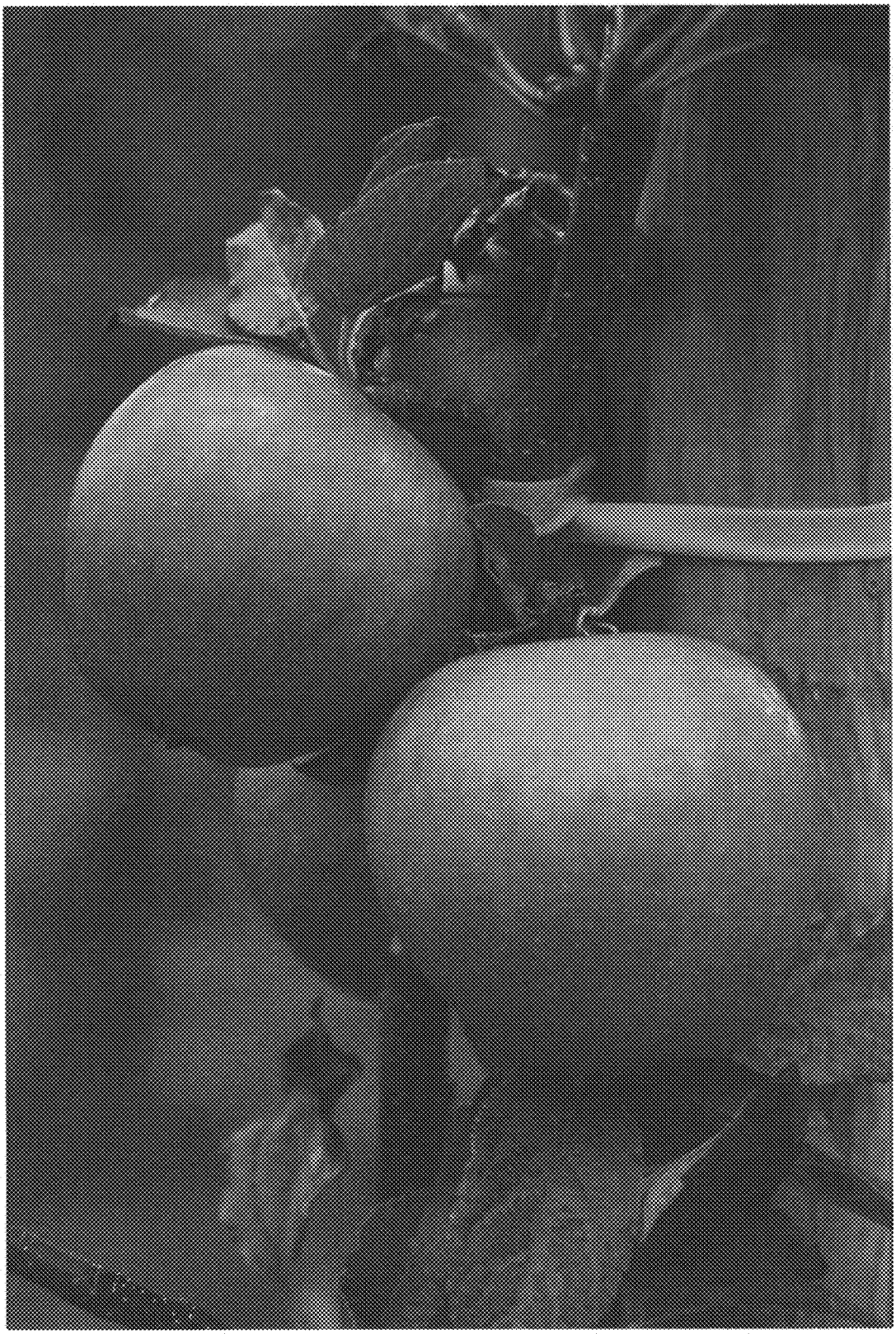
FIG. 3 further illustrates fruits of apple tree variety 'SunSpark' prior to harvest.
Figure 4:
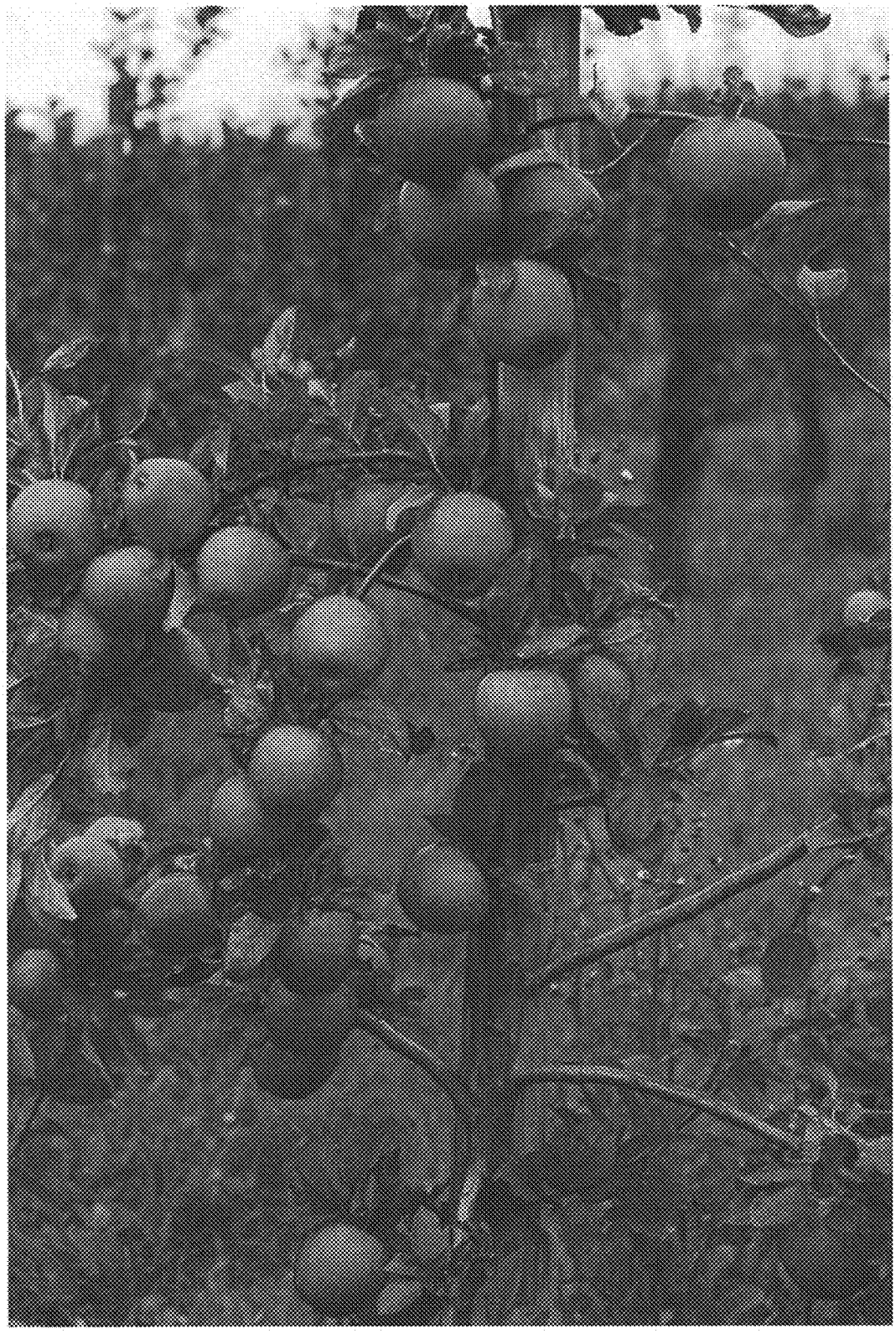
FIG. 4 illustrates a tree of apple tree variety 'SunSpark' with fruit on the tree.
Figure 5:
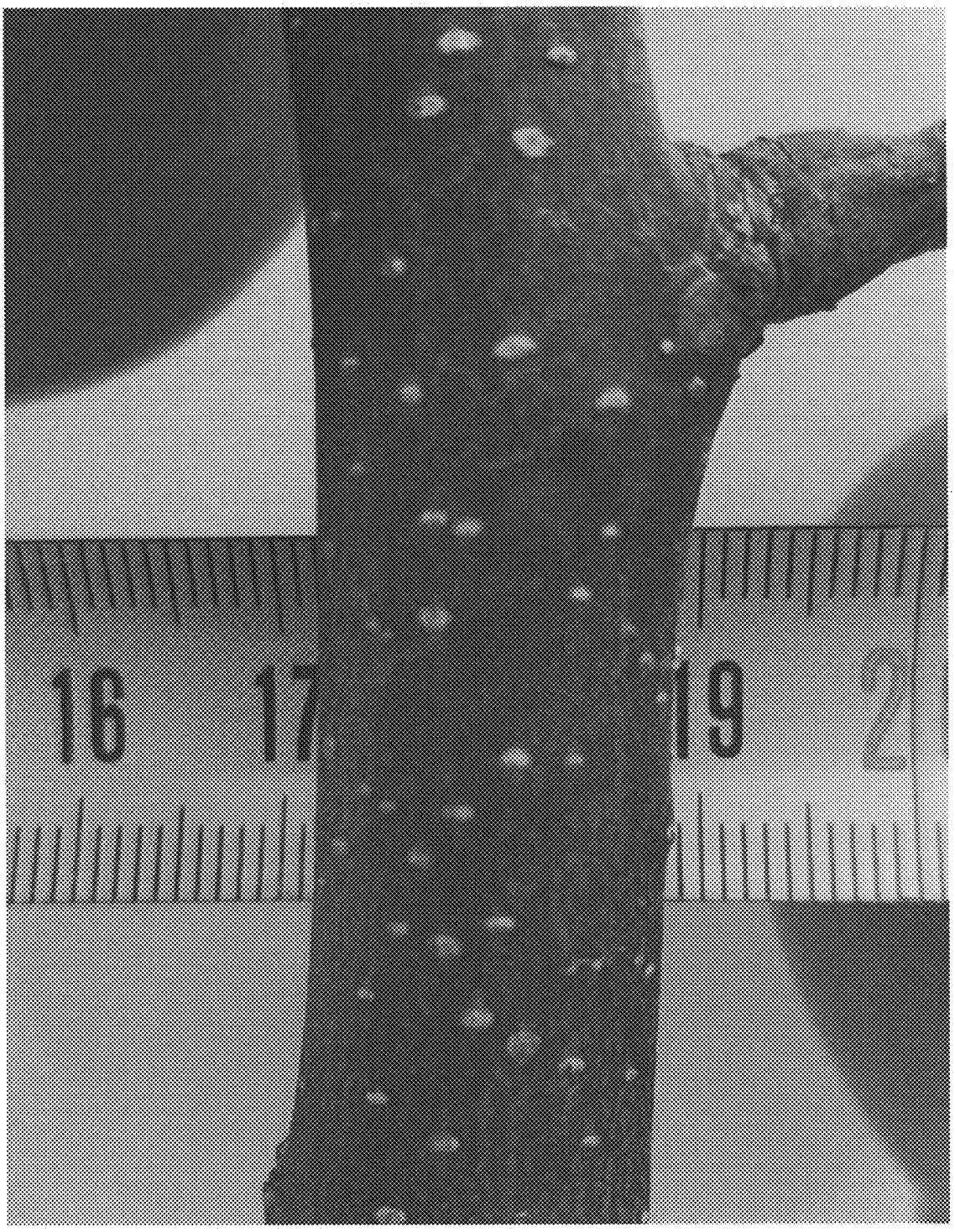
FIG. 5 illustrates a trunk of apple tree variety 'SunSpark' with trunk bark lenticels.
Figure 6:
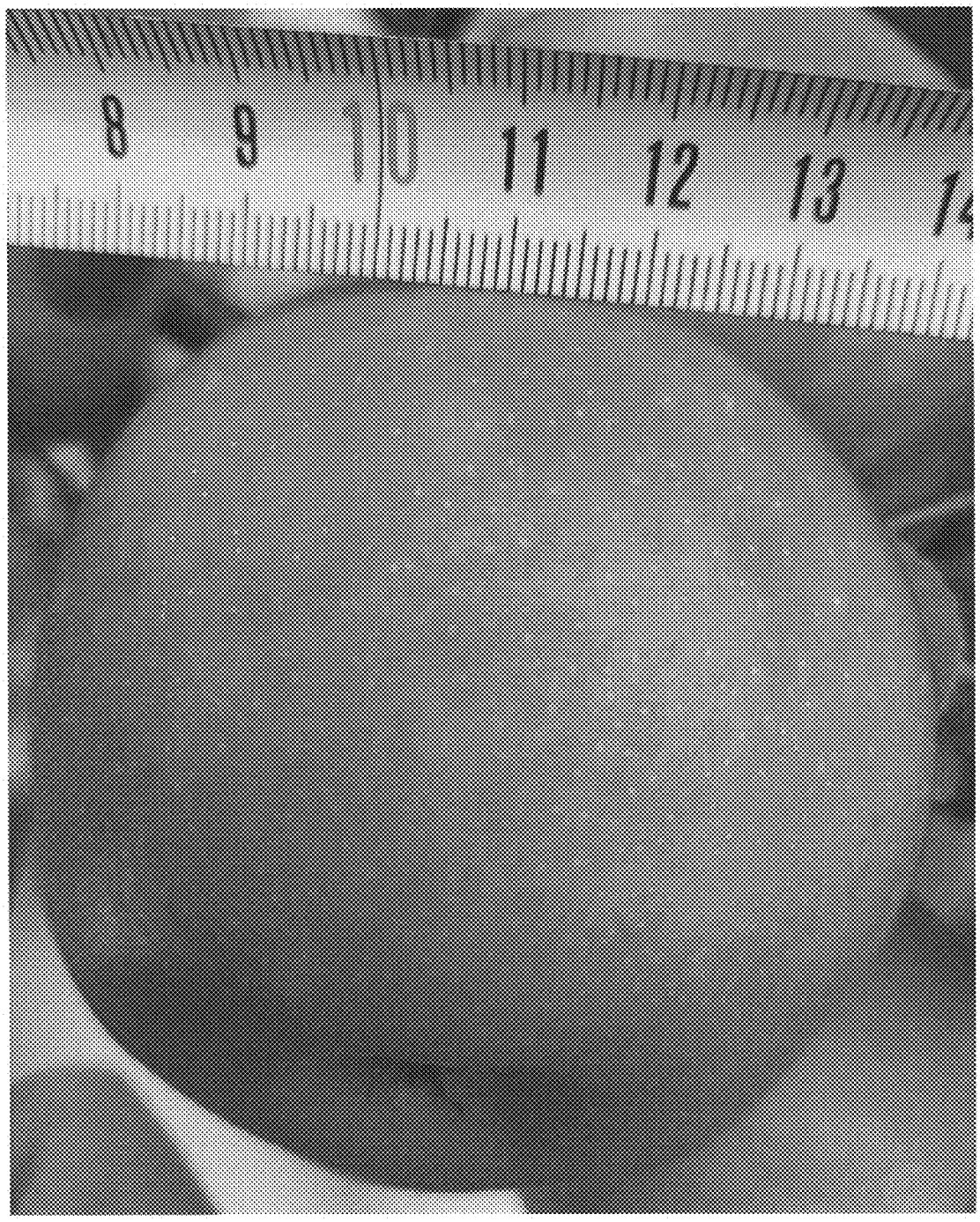
FIG. 6 further illustrates a fruit of apple tree variety 'SunSpark' with fruit skin lenticels.

The following description sets forth the distinctive characteristics of 'SunSpark'. The following botanical description of 'SunSpark' is based on observations of the originally identified tree, and asexually reproduced progeny. Unless otherwise indicated, the descriptions are from trees that are 3 years old grown in Geldermalsen, The Netherlands.

Certain characteristics, as well as the phenotype, of this variety may vary with changing environmental conditions (e.g., light, temperature, moisture, etc.), nutrient availability, or other factors. Quantified measurements are expressed as an average of measurements taken from 20 individual plants of the new variety grown and observed in the apple variety test location in Geldermalsen, The Netherlands. Trees were observed in the third year ($2^{nd}$ yield) on M9 rootstock. The measurements of any individual plant, or any group of plants, of the new variety may vary from the stated average. Color descriptions and other terminology are used in accordance with their ordinary dictionary descriptions, unless the context clearly indicates otherwise. All color references are from The RHS Colour Chart of The Royal Horticultural Society of London (RHS) (Sixth Edition, 2015).

Tree:

*Type.*—Ramified.

*Overall shape.*—Spreading.

*Vigor.*—Medium.

*Height.*—Approximately 2.60 m.

*Width.*—Approximately 1.00 m.

*Caliper.*—Approximately 40 mm on average at 500 mm above the graft union in 3-year-old trees on M9 rootstock.

*Trunk bark texture.*—Smooth, with prominent lenticels, oriented horizontally.

*Trunk bark lenticels.*—3 to 5 per square centimeter. Shape: Oval. Color: RHS 156A (color description: Greyed-White), Size: Approximately 0.5 mm long by approximately 1.0 mm wide.

*Trunk bark color.*—RHS 200B (color description: Brown).

*Primary branches.*—Angle: As trained, moderately flat to near flat, ranging from 75 to 85 degrees from vertical. The typical and observed lateral branch length is 50 cm.

*Size.*—Ranges from 1.8 cm to 3.4 cm in diameter with an average of 2.7 cm (as measured 10 cm from the trunk, first primary branch above the graft union and arising from the main stem).

*Branch color.*—One-year old branches are RHS 200D (color description: Brown while older branches are RHS 200B (color description: Brown).

*Branch pubescence.*—Absent.

*Branch direction.*—Slightly upwards, spreading. In nursery stage, horizontal.

*Branch lenticels.*—Approximately 3 per square cm. Shape: Round and elongated.

*Color.*—RHS 198C (color description: Greyed-Green). Size: Approximately 0.5 mm long by approximately 1.0 mm wide.

*Branch surface texture.*—Smooth.

*Internodes.*—Average internode length is approximately 4 cm for a one-year-old shoot.

*Bearing.*—On spurs, beginning on two-year-old wood.

*Hardiness.*—European Zone 6 hardy. No frost injuries or problems were observed at the testing location during the winter period in Northwest Europe.

*Disease and insect resistance observations.*—

*Sensitivity to pest/disease.*—Medium susceptible to powdery apple mildew (*Podosphaera leucotricha*) compared to 'Gala' (unpatented) and 'Jonagold' (unpatented). Sensitivity to black scab (*Venturia inaequalis*) is much less compared to 'Gala' (unpatented) and 'Jonagold' (unpatented). Sensitivity to *Neonectria ditissima* (apple tree canker) is less compared to 'Gala' (unpatented). Other diseases occurring in the local area have not been observed on this variety. Sensitivity to insects: no known resistance to insects.

Leaves:

*Shape.*—The overall leaf shape is elliptical-elongated, rounded at the base.

*Texture.*—Upper surface: Smooth. Lower surface: Uneven/rough.

*Pubescence.*—Upper surface: Smooth. Lower surface: Slightly pubescent.

*Sheen.*—Glossy with a high sheen.

*Length.*—130 mm.

*Width.*—40 mm.

*Margin.*—Serrate, with bi-serrate regions. Approximately 30 mm long and 5 mm wide.

*Tip* (*apex*).—The apex shape is acuminate (Acute). The apex margin is serrate. The apex surface texture is smooth with absent pubescence on the upper surface and weak/slightly pubescent on the lower surface.

*Stipules.*—Relatively wide, present on most petioles. Length: Average 5 mm. Width: Average 1.6 mm at base. Upper surface texture: Smooth. Lower surface texture: Slightly pubescent. Apex shape: Acicula. Color: RHS 138B (color description: Green).

*Leaf color.*—Upper surface: RHS 137A (color description: Green). Lower surface: RHS 138B (color description: Green).

*Leaf vein color.*—RHS 138B (color description: Green).

*Petiole length.*—18 mm.

*Petiole diameter.*—About 1.8 mm.

*Petiole color.*—RHS N81A (color description: Purple-Violet).

Flower:

*General.*—Pentamerous. Size: 32 mm in length (±2.0 mm), and 18 mm wide (±2.0 mm). Diameter: Approximately 37 mm when fully flattened. Flower depth (height of the corolla): about 14-15 mm, measured when the flowers are fully open. Shape: Radially symmetrical-rotate (actinomorphic).

*Flower bud.*—Shape: Obtuse shape. Length: 9.5 mm. (±1.0 mm). Diameter: 4.8 mm. (±0.3 mm). Color: Unopened bud: RHS 178B (color description: Greyed-Red). Opened bud: RHS N144A (color description: Yellow-Green).

*Petals.*—Number: 5 per flower. Length: 22 mm. Width: 13.5 mm. Shape: The overall petal shape is elliptic. The apex is acuminate/obtuse, rounded at the base. Margin type: Ascendingly imbricate. Margin texture: Upper surface: smooth. Lower surface: smooth. Arrangement: Valvate, some petals overlap each other. Color: Upper petal surface: RHS N155B (color description: White) with a color gradient to red-purple RHS 63B (color description: Red-Purple) at the base. Lower petal surface: RHS N155B (color description: White) to RHS 63B (color description: Red-Purple) at the base. Flower color: Primarily RHS 155D (color description: White), when petals fully opened, undersides of petals have shades of RHS 67A (color description: Red-Purple). In the balloon stage the color is RHS 55A (color description: Red).

*Sepals.*—Number: 5 per flower. Shape: Cordate. Apex: Acuminate. Base: Broad. Margin type: entire hairy. Length: 9 mm. Width: 4.5 mm. Color (upper surface): RHS 143B (color description: Green). Color (lower surface): RHS 143C (color description: Green). Arrangement: Valvate.

*Pedicel/Peduncle.*—Apples do not have branched inflorescences, and hence do not have pedicels. The flower stalk of an apple is the peduncle. Length: 18 mm. Diameter: 2 mm. Color: RHS N144A (color description: Yellow-Green).

*Stamen.*—Number: Approximately 20 per flower, radial symmetry. Length: 11 mm. Filament color: RHS 155C (color description: White).

*Anthers.*—Number: About 20 per flower. Color: RHS 155B (color description: White). Unopened anther color: RHS 4D (color description: Yellow). Pollen color: RHS 4C (color description: Yellow). Amount of pollen produced: moderate.

*Pistil.*—General: In the middle of the flower with 5 styles. Fruit develops from multiple fused carpels. Inferior ovary. Length: 12 mm. Number: Typically 5 pistils per flower. Arrangement in flower: Radial. Color: RHS 151C (color description: Yellow-Green). Color of stigma: RHS 4C (color description: Yellow). Color of styles: RHS 151B (color description: Yellow-Green). Ovary length: 8.0 mm. Ovary color: RHS 149B (color description: Light Green).

*Pollination requirements.*—'SunSpark' is diploid, SS alleles S5 S24. Ornamental apple varieties such as 'Everest' (unpatented), 'Golden Hornet' (unpatented) and Professor Sprenger (unpatented) are suitable pollinators. Other medium-late flowering commercial apple varieties, suitable for cross pollination, are not tested yet.

*Fragrance.*—Sweet apple blossom.

*Bloom season* (*time of beginning of flowering*).—Medium to late. Location Geldermalsen, The Netherlands. Observation in 2020. Start of flowering: April 16. Full bloom: April 23. End of flowering: May 1.

Fruit:

*General.*—Measurements are the average of 20 typical 'SunSpark' apples. Size: Medium. Length: Approximately 70 mm. Width: Approximately 78 mm. Shape: Oblate conical. Roundly oblate/conical, slightly irregular, no ribbing or lobes, Shape of base: Concave. Shape of apex: Truncate. Calyx: persistent, mostly closed. Calyx tube: Conic. Individual fruit weight (average): 231 g. Basin: Shape: Concave. Width: Approximately 27 mm. Depth: Approximately 8 mm. Cavity: Width: Approximately 23 mm. Depth: Approximately 17 mm.

*Fruit stem.*—Length: Approximately 18 mm. Diameter: Approximately 2 mm. Color: RHS N144A (color description: Yellow-Green). Locules: 5. Length: Approximately 17 mm. Width: Approximately 11 mm.

*Fruit skin.*—Tendency to crack: No fruit or stem cracks observed during the testing period. Thickness: Relatively thin. Surface texture: Smooth. Lenticels: Prominently visible, average 4 lenticels per $cm^2$, more pronounced towards the calyx end of the fruit. Diameter: Approximately 0.4 mm. Length: 0.8 mm. Shape: Round. Color: RHS N155A (color description: White). Color: General color effect: RHS 45B (color description: Red). Ground color: varies from RHS 1B (color description: Green-Yellow) up to RHS 13A (color description: Yellow). Over color: Orange red (with bloom removed). Skin front color varies from RHS N30A (color description: Orange-Red) up to RHS 45B (color description: Red) on front side, Skin background color varies from RHS 1B (color description: Green-Yellow) up to RHS 13A (color description: Yellow). Pattern of over color: Flushed and mottled. Relative area of over color: Medium. 70% up to 90% of the fruits. Width of fruit stripes: 2 mm. Russeting: Golden russet, in stem cavity, Color: REIS 161A (color description: Greyed-Yellow). Bloom: Generally no visible bloom or coating on the fruit skin; some fruits in the shade of the tree have a slight bloom on the fruit skin.

*Flesh.*—Flavor: Sub-acid with a sweet hue. Brix: Between 13.6° and 15.3° at harvest. Juiciness: Very juicy. Color: RHS 10C (color description: Yellow). Aroma: mild aroma with a sweet hue that is a unique and distinguishing characteristic of 'SunSpark'. Firmness: Between 8 and 9 kg/cm$^2$ at harvest. Crunchy bite. Core: Core position is considered median; core line position is basal; core shape is flat conical; 5 carpels per fruit; shape (carpels in the core) is elliptical. Diameter of core: Approximately 40 mm. Number of bundles: Approximately 5 per fruit. Core length: Approximately 30 mm. Locules: Length: 16 mm. Width: 7 mm, the form is fully open. Calyx tube length: Approximately 58 mm (measured as the length from the calyx end at the point of sepal attachment to the point of calyx tube closure).

*Seed.*—Number: About 2 per cell. Shape: Acute/oval. Length: Approximately 8 mm. Width: Approximately 4 mm. Texture: smooth surface. Color: RHS 175A (color description: Greyed-Orange).

*Fruit production.*—Production is moderate to heavy with a tendency to alternate bearing, therefore fruit thinning is necessary. The mature harvest date is end of September/early October at the location of observation. Repeat pickings (2-3) are required to meet with the fruit quality standards. Harvest dates on the location were first pick (70% of all fruits) on Sep. 29, 2020 and second pick (remaining 30% of all fruits) on Oct. 15, 2020. Harvest window is in a wide range of about three weeks. Fruit does not drop prematurely or after the optimum harvest period.

*Time of fruit eating maturity.*—Medium. After harvest a cold storage period of 3-4 weeks is recommended to develop the typical taste of 'SunSpark'. Storability: Retains quality and texture for up to 7 months in ULO conditions (1° C., 1.2% $O_2$, 0.7% $CO_2$), as shown by storage trials over 2 seasons at the location of observation.

*Minimum fruit quality parameters.*—Firmness 7 kg/cm$^2$, 13° Brix, diameter 65 mm and fruit weight 120 g.

*Usage.*—Fresh market. Excellent dessert apple.

*Storage.*—Very good storability (Tested in The Netherlands, season 2018-2019). At harvest, fruits of 'SunSpark' had a firmness between 8-9 kg/cm$^2$ and Brix levels between 13.6° to 15.3°. At harvest, some fruits (4 of 20) showed watercore. After storage until February, firmness from fruits stored in RA (normal room atmosphere) conditions was ±1 kg/cm$^2$ lower than at harvest. In May, firmness in RA had further dropped to 7.8 kg/cm$^2$ and 7.0 kg/cm$^2$ after 1 week at room temperature of 20° C. Fruit stored in ULO conditions (1° C., 1.2% $O_2$, 0.7% $CO_2$) until February and even May had no decrease of firmness. There is no difference between the firmness of fruits stored at 1° C. or at 3° C. There is no effect of 1-mcp (1-methylcyclopropene) (SmartFresh), not even after one week of shelf life. The several storage regimes had no influence on the Brix levels of the fruits.

*Shipping quality of fruit.*—Excellent, not sensitive to bruising. during routine picking and handling procedures.

*Productivity of fruit.*—About 8 kilograms for a 3-year-old tree.

COMPARISON TO PARENTAL AND SIMILAR VARIETIES

The new distinctive apple variety named 'SunSpark' is distinguished by its intense and nearly full color, internal indices in combination with a crunchy bite, specific flavor and excellent storage and shelf-life, which are different than its parents. Additionally, fruit appearance is distinctly different than that of the parental variety 'Nicoter' (U.S. Plant Pat. No. 17,201). Fruit quality aspects like flavor, taste and texture are distinctly different than that of the parental variety 'Honeycrisp' (U.S. Plant Pat. No. 7,197).

Two similar commercial apple varieties to compare the distinct features of 'SunSpark' are 'Gala' (unpatented) and 'Jonagold' (unpatented).

'SunSpark' most closely resembles 'Gala' (unpatented) in appearance ('Nicoter' (U.S. Plant Pat. No. 17,201) is also originated of a 'Gala' (unpatented) cross). The fruit of 'SunSpark' is less conical in shape and bigger in fruit size than that of 'Gala' (unpatented) and the coloration is a different red than that of 'Gala' (unpatented) with more pronounced lenticels.

'SunSpark' closely resembles 'Jonagold' (unpatented) in relation to tree shape and fruit maturation date. Fruit quality parameters of 'Jonagold' (unpatented), such as taste, texture and flavor, are distinctly different compared to 'SunSpark'.

What is claimed is:

1. A new and distinct variety of apple tree named 'SunSpark' as shown and described herein.

* * * * *